(12) United States Patent
Gonzalez et al.

(10) Patent No.: US 9,655,701 B2
(45) Date of Patent: May 23, 2017

(54) DENTAL ACCESSORY

(71) Applicant: Sunstar Americas, Inc., Chicago, IL (US)

(72) Inventors: Leoncio Angel Gonzalez, Winfield, IL (US); Russell G. Kalbfeld, Naperville, IL (US); Yuet Ping Yao, Yuen Long (CN)

(73) Assignee: MOTOROLA SOLUTIONS, INC., Schaumburg, IL (US)

( * ) Notice: Subject to any disclaimer, the term of this patent is extended or adjusted under 35 U.S.C. 154(b) by 162 days.

(21) Appl. No.: 14/400,621

(22) PCT Filed: Jul. 25, 2014

(86) PCT No.: PCT/CN2014/083025
§ 371 (c)(1),
(2) Date: Nov. 12, 2014

(87) PCT Pub. No.: WO2016/011660
PCT Pub. Date: Jan. 28, 2016

(65) Prior Publication Data
US 2016/0193022 A1   Jul. 7, 2016

(51) Int. Cl.
*A61C 3/06* (2006.01)
*A61C 17/00* (2006.01)
*A61C 17/24* (2006.01)
*A61C 1/12* (2006.01)
*A61C 17/22* (2006.01)

(52) U.S. Cl.
CPC .............. *A61C 17/005* (2013.01); *A61C 1/12* (2013.01); *A61C 17/22* (2013.01); *A61C 17/24* (2013.01)

(58) Field of Classification Search
CPC ....... A61C 17/005; A61C 17/24; A61C 17/22; A61C 1/12
See application file for complete search history.

(56) References Cited

U.S. PATENT DOCUMENTS

| | | |
|---|---|---|
| 3,599,333 A | 8/1971 | Muhler |
| 4,055,897 A | 11/1977 | Brix |
| 4,259,071 A | 3/1981 | Warden et al. |
| 4,486,175 A | 12/1984 | Fisher et al. |
| 4,929,180 A | 5/1990 | Moreschini |
| 5,083,922 A | 1/1992 | Yale |

(Continued)

FOREIGN PATENT DOCUMENTS

| | | |
|---|---|---|
| EP | 0530646 | 3/1993 |
| GB | 498423 | 1/1939 |
| WO | 2005004746 | 1/2005 |

OTHER PUBLICATIONS

Jefferies, S.R.; "Abrasive Finishing and Polishing in Restorative Dentistry: A State-of-the-Art Review," The Dental Clinics of North America 51, 2007, pp. 379-397.

(Continued)

*Primary Examiner* — Glenn Richman
(74) *Attorney, Agent, or Firm* — Michael Best & Friedrich LLP

(57) ABSTRACT

A prophylaxis angle that is configured to be attached to and operated by a powered dental handpiece. The prophylaxis angle includes a cup having a first end and a second end. The first end is couplable to the dental handpiece and at least one projection is at the second end of the cup.

29 Claims, 8 Drawing Sheets

(56) References Cited

U.S. PATENT DOCUMENTS

| | | |
|---|---|---|
| 5,178,538 A | 1/1993 | Eckert |
| 5,334,020 A | 8/1994 | Eckert |
| 5,380,202 A | 1/1995 | Brahler |
| 5,405,265 A | 4/1995 | Mendoza |
| 5,482,461 A | 1/1996 | Yale |
| D368,523 S | 4/1996 | Mendoza |
| 5,797,744 A | 8/1998 | Rosenberg |
| D413,384 S | 8/1999 | Hanley et al. |
| 7,024,717 B2 | 4/2006 | Hilscher et al. |
| 7,101,182 B2 | 9/2006 | Garrison et al. |
| 7,678,314 B1 | 3/2010 | Eckert |
| 7,806,689 B2 | 10/2010 | Lee et al. |
| 7,955,079 B2 | 6/2011 | Chronister et al. |
| 8,123,523 B2 * | 2/2012 | Carron ................. A61C 17/005 433/125 |
| 8,360,774 B2 * | 1/2013 | Carron ................. A61C 17/005 433/125 |
| 8,387,196 B2 | 3/2013 | Jimenez et al. |
| 8,591,231 B1 * | 11/2013 | Wolske ................. A61C 17/005 433/125 |
| 8,597,022 B2 * | 12/2013 | Carron ................. A61C 17/005 433/114 |
| 8,784,102 B1 | 7/2014 | Kumar |
| 2004/0131994 A1 | 7/2004 | Bachmann et al. |
| 2009/0081609 A1 | 3/2009 | Kalbfeld et al. |
| 2012/0107769 A1 | 5/2012 | Chronister et al. |
| 2013/0149666 A1 | 6/2013 | Chalifoux |
| 2014/0017630 A1 | 1/2014 | Chalifoux |

OTHER PUBLICATIONS

Navajo Brand® Pumice, CR Minerals Co., available at <http://www.groshea.com/pdf/CR%20Minerals/Tech%20Data%Sheet%20Granular%20Grades.pdf> downloaded Feb. 3, 2015, (2 pages).

Prophy Cups & Brushes, Young, available at <http://www.youngdental.com/product-cat/prophy-cups-brushes/>, downloaded Feb. 3, 2015, (3 pages).

Contra Elite Disposable Prophy Angles, Young Dental Products, available at <http://www.prestigedentalproducts.com/Contra-Elite-Disposable-Prophy-Angles-Young-Dental/>, downloaded Feb. 3, 2015, (2 pages).

Paste Free Prophy Angles (Butler), available at <http://www.prestigedentalproducts.com/Paste-Free-Prophy-Angles-Butler/?printable=Y>, downloaded Feb. 3, 2015, (2 pages).

International Search Report and Written Opinion for Application No. PCT/CN2014/083025 dated Apr. 29, 2015 (14 pages).

* cited by examiner

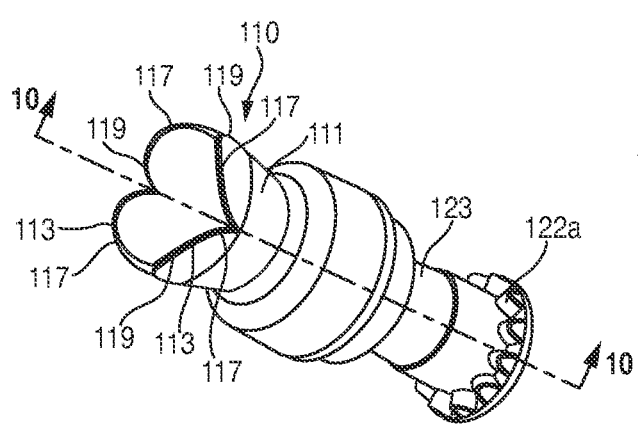
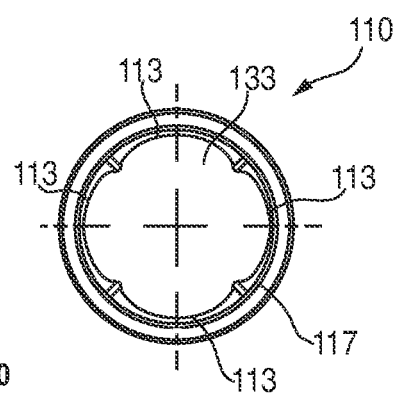
Fig. 8  Fig. 9
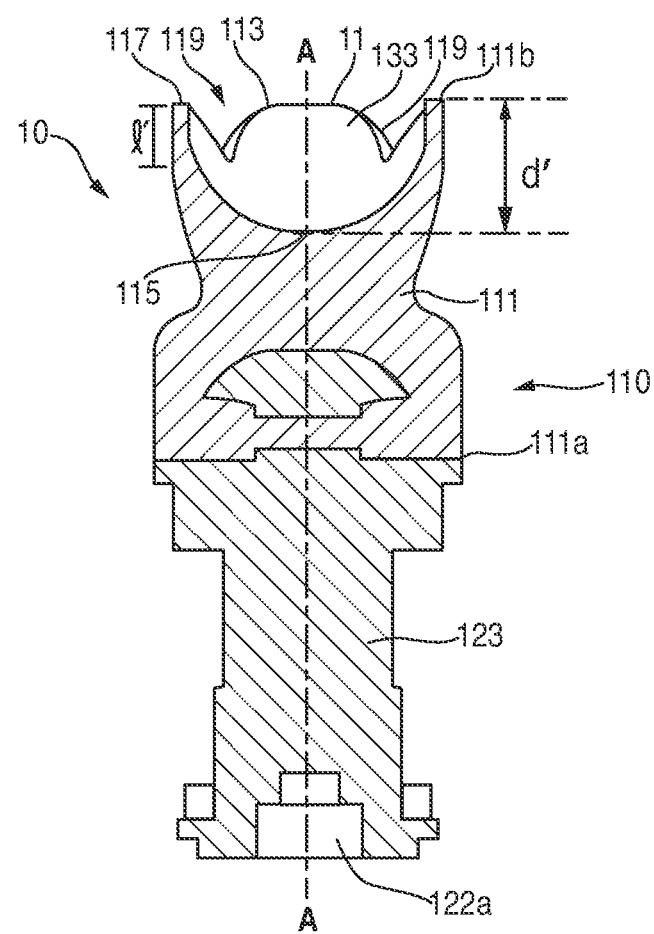
Fig. 10

DENTAL ACCESSORY

BACKGROUND

The present invention relates to a dental accessory for cleaning and polishing of teeth, particularly a dental accessory commonly called a "prophylaxis cup" or "prophy cup," which is normally mounted for use on either a disposable prophy angle or an autoclavable prophy angle. The prophylaxis angle is configured to be drivingly coupled to a powered dental handpiece.

Conventional disposable or autoclavable prophy angles used by dental professionals to polish teeth include a generally tubular housing and a cup attached to one end of the housing that holds a cleaning paste. The cup, when filled with paste, is pressed against the tooth surfaces to clean and polish teeth.

Conventional prophy cups are generally adequate for polishing teeth, but are not very effective at reaching under the gumline where it is important to clean. Further, prophy pastes can be abrasive and uncomfortable to the user. Prophy pastes also require dental professionals to continuously dip the prophy cup into a cup of paste while performing a cleaning. Thus, there is a need for an improved prophy cup for disposable and autoclavable prophy angles that can more effectively reach under the gumline and avoid the need to use prophy paste.

SUMMARY

A cup for a prophylaxis angle is provided. The prophylaxis angle is configured to be attached to and operated by a powered dental handpiece. The cup includes a first end and a second end. The first end is couplable to the dental handpiece. The second end includes or terminates in at least one projection. The cup also includes an inner surface and an abrasive material on the inner surface.

A method of manufacturing a prophylaxis cup includes forming the prophylaxis cup and pressing an inner surface of the prophylaxis cup into the abrasive material so that the abrasive material is retained on at least a portion of the inner surface of the cup.

BRIEF DESCRIPTION OF THE DRAWINGS

FIG. 4 is a top view of the prophy cup of FIG. 3a.

FIG. 5 is a cross-sectional view of the prophy cup and shaft of FIG. 3a through line 5-5 of FIG. 3a.

FIG. 8 is a perspective view of a prophy cup attached to a shaft having a gear according to a second embodiment of the invention.

FIG. 9 is a top view of the prophy cup and shaft of FIG. 8.

FIG. 10 is a cross-sectional view of the prophy cup of FIG. 8 through line 10-10 of FIG. 8.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

DETAILED DESCRIPTION

Figure 1:
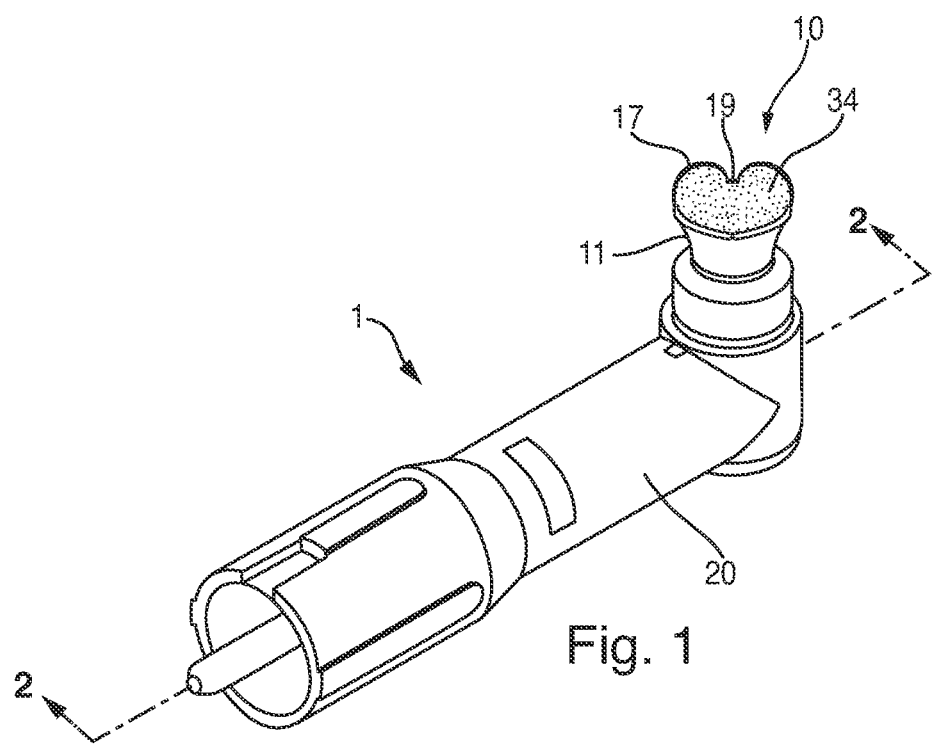
FIG. 1 is a perspective view of a prophy angle according to one embodiment of the invention, the prophy angle including a prophy cup.
Figure 2:
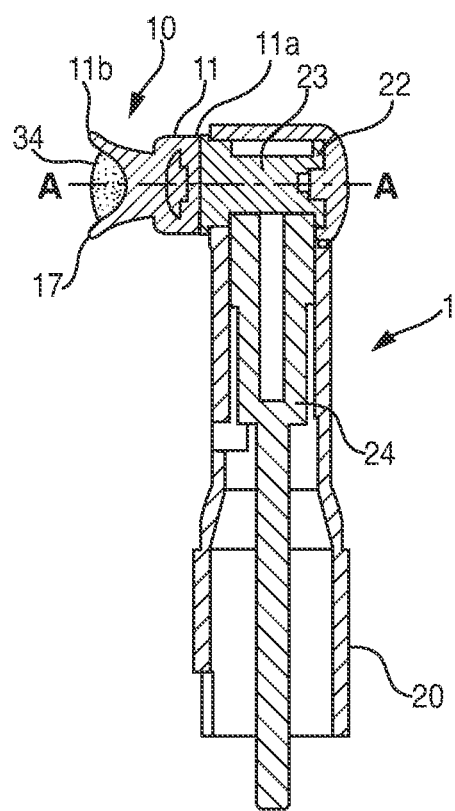
FIG. 2 is a cross-sectional view of the prophy angle through line 2-2 of FIG. 1.
Figure 3A:
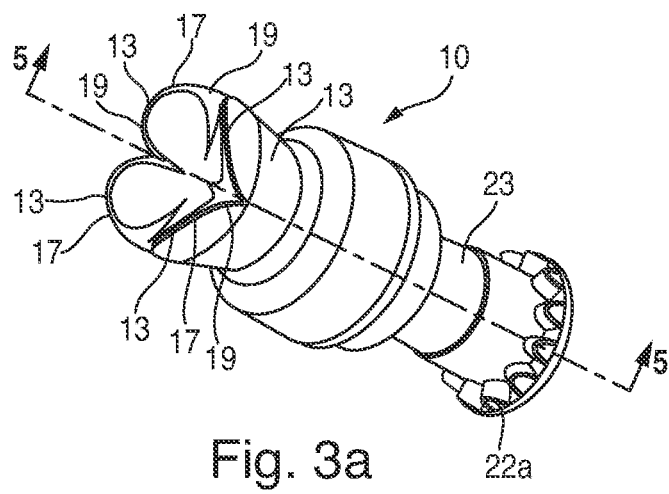
FIG. 3a is a perspective view of the prophy cup of FIGS. 1 and 2 attached to a shaft having a gear.
Figure 3B:
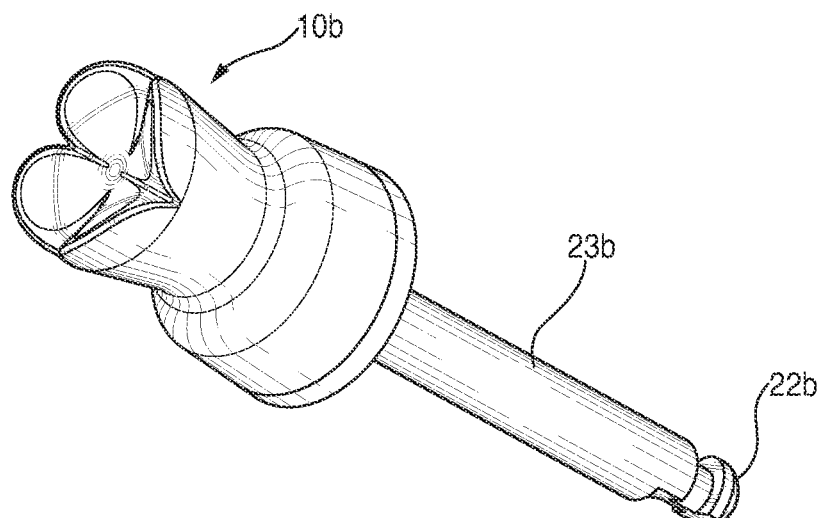
FIG. 3b is a perspective view of the prophy cup of FIGS. 1 and 2 attached to a shaft having a latch.
Figure 3C:
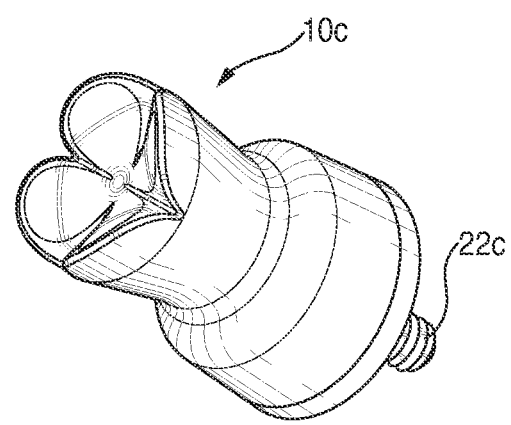
FIG. 3c is a perspective view of the prophy cup of FIGS. 1 and 2 attached to a shaft having a screw.
Figure 6:
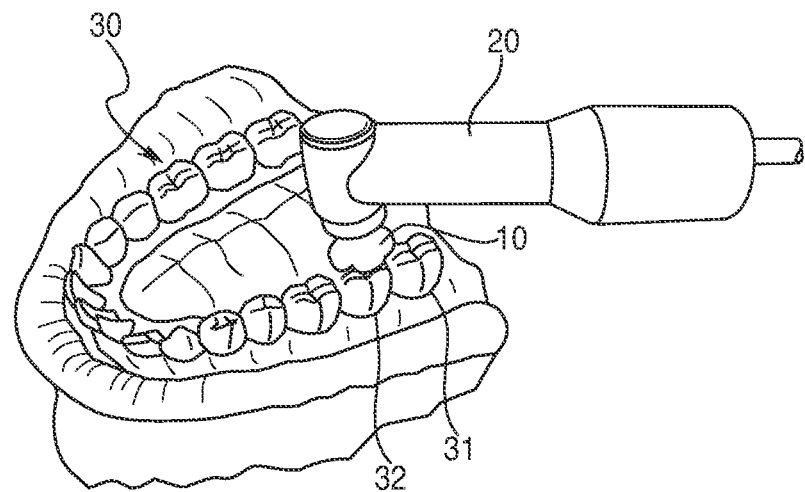
FIG. 6 is a perspective view of the prophy angle of FIGS. 1 and 2 being used on teeth.
Figure 7:
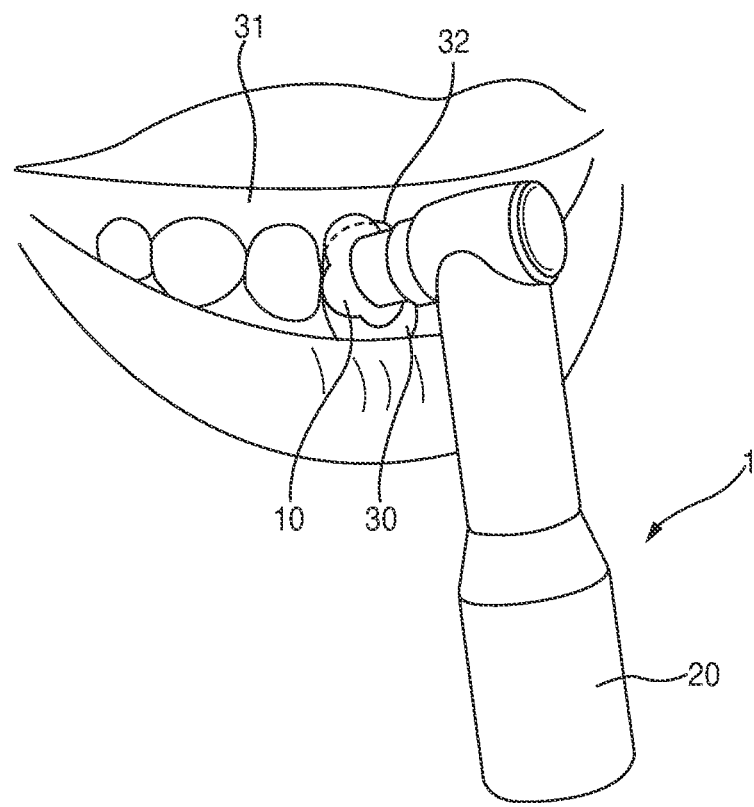
FIG. 7 is a perspective view of the prophy angle of FIGS. 1 and 2 being used under the gumline.

A "prophylaxis angle" or "prophy angle" 1 includes a housing 20 and a drive shaft 24, which is attached to a powered dental handpiece (not shown). A prophy cup 10 is rotatably mounted to the prophylaxis angle 1. In particular, the prophy cup is connected to a shaft 23, such as by overmolding the cup 10 onto the shaft 23. FIGS. 3a and 8 illustrate a shaft 23 that terminates in a gear 22a, which are generally included in disposable prophy angles. FIGS. 3b and 3c each illustrate a shaft 23 that terminates in a latch 22b (FIG. 3b) or a screw 22c (FIG. 3c), either of which are used with autoclavable prophy angles, as is commonly known in the art. In other configurations, the prophy cup is couplable to the powered dental handpiece by a pressure fitting snap and button configuration (not shown). In each application, the shaft 23 is configured to be rotatably coupled ultimately to the dental handpiece. In use, while the cup 10 is applied to a tooth 30, the handpiece rotates the drive shaft 24 of the prophy angle 1, which causes rotation of the shaft 23 and the prophy cup 10. The cup 10 polishes the tooth 30 while the cup 10 rotates.

In the embodiment of FIGS. 1-7, the prophy cup 10 defines a longitudinal axis A and includes a wall 11 that defines a periphery of the cup 10. The wall 11 is symmetrical about the longitudinal axis A and defines a first end 11a and a second end 11b of the cup 10. The portion of the wall 11 terminating at the first end 11a is generally cylindrical and the portion of the wall 11 terminating at the second end 11b is a generally truncated cone. In the illustrated embodiment, the second end 11b has a diameter of approximately 6-7 mm. However, in other embodiments the prophy cup 10 may be defined by other suitable shapes and/or have other dimensions.

At least one projection 17 is at the second end 11b. In the embodiment of the FIGS. 1-7, the multiple projections 17 are separated by one or more slots or recesses 19 extending approximately longitudinally from the second end 11b and may be evenly disposed around a circumference of the cup 10. As shown in FIGS. 1-5, each of the projections 17 have a generally scalloped or arcuately-shaped distal edge 13 so that the cup resembles the shape of a clover as viewed in FIG. 4. The projections 17 preferably flare radially outwards and away from the longitudinal axis A. Advantageously, the projections 17 are sized to be thin and flexible enough to fit comfortably between the tooth 30 and the surrounding gum 31 and under the gumline 32 when the cup 10 is pressed against the surface of the tooth 30 during cleaning. In the exemplary embodiment of FIGS. 2-5, the length l of each recess 19 is approximately 1-2 mm while the depth d of the cup to a center 15 of the cup 10 is approximately 1-2 mm. Because of the recesses and scalloped shape of the projections 17, the distal edge 13 of the second end 11b of the cup 10 is not within a single plane.

An abrasive material 34 is applied in a manner described hereafter to at least a portion of an inner surface 33 of the prophy cup 10. A substantial portion of the abrasive material remains exposed on the surface 33 to enhance the polishing of the teeth. According to a preferred embodiment of the invention, the abrasive material is pumice. The pumice may range from processed grade 4/0 to grade 3, which includes particle sizes from 44-845 microns. Preferably, the pumice is from processed grade 0½, which includes particle sizes from 44 to 250 microns. It should be understood that other abrasive materials having similar particle sizes may be used in place of pumice. For example, the abrasive material could also be perlite, aluminum oxide, aluminum-silicate, chalk, corundum, cuttle, diamond, emery, feldspar, garnet, Kieselguhr, quartz, silica, silicon carbide, sodium-potassium, tin oxide, Tripoli, zirconium silicate, a combination thereof, or any other suitable abrasive material. As a result of the inner surface 33 including the abrasive material 34, the inner surface 33 has a slightly textured or non-smooth surface.

The prophy cup 10 is preferably formed from any suitable thermoplastic elastomer (TPE), but it may also be formed from other suitable soft materials. Such soft materials might, in appropriate circumstances, include a silicone. The prophy cup 10 may be formed by an injection molding process, for example, although the prophy cup may be formed by any suitable process. For example, the prophy cup 10 may be heated to a predetermined temperature at which point the prophy cup 10 sufficiently softens such that when pressing the prophy cup 10 into the abrasive material, at least a portion of the inner surface receives and retains the abrasive material in additional or alternative embodiments, an adhesive material 34 may be applied to at least a portion of the inner surface 33 such that when pressing the prophy cup 10, including projections 17, into the abrasive material 34, the adhesive material receives and retains the abrasive material. The adhesive material may be any suitable material for use in the mouth, and the material should preferably retain the abrasive material 34 under the parameters of standard stability tests. The adhesive material may include, for example, heat curing adhesives (i.e., urethanes, polyamides, epoxies), acrylic based ultraviolet (UV) cured adhesives, cyanoacrylate, urethanes, solvent based elastic polymer adhesives, and ethylene-vinyl acetate based hot melt adhesives. By either the heating or adhesive method, at least a portion of the inner surface 33 of the prophy cup 10 retains the abrasive material 34. This results in the inner surface 33 of the prophy cup being textured or at least partially non-smooth so as to provide a suitably abrasive surface to polish teeth. In a preferred embodiment, the abrasive material is retained on the projections 17. However, in other embodiments, the abrasive material is retained on the entire inner surface 33 of the prophy cup 10 or any suitable percentage of the inner surface 33.

To use the prophy angle 1, a dental professional, such as a hygienist or dentist, attaches the prophy angle to a motorized dental handpiece (not shown). After activating the handpiece to begin rotation of the prophy cup 10, the rotating prophy cup 10 is moved along a patient's teeth to effectuate cleaning and polishing. As the prophy cup 10 is pressed on the teeth, the projections 17 flare further outwards, allowing the prophy cup 10 to reach under the gumline 32. Unlike conventional prophy angles, the prophy angle described herein does not require a paste to effectuate cleaning, due to the abrasive material 34 retained on the inner surface 33 of the prophy cup 10.

The prophy cup shown in FIGS. 1-7 and described above, is merely exemplary. In alternative embodiments, the prophy cup may have alternative configurations including projections and recesses of any suitable size, number, and shape. FIGS. 8-13 illustrate alternative embodiments of the cup 10 of FIGS. 1-7. The prophy cups 110, 210, 310, 410 of FIGS. 8-13 are substantially similar to the prophy cup 10 of FIGS. 1-8 and therefore, only the differences will be discussed herein.

Figure 4:
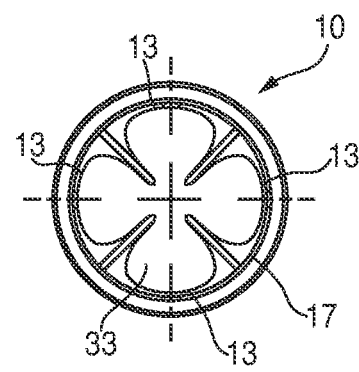
Figure 5:
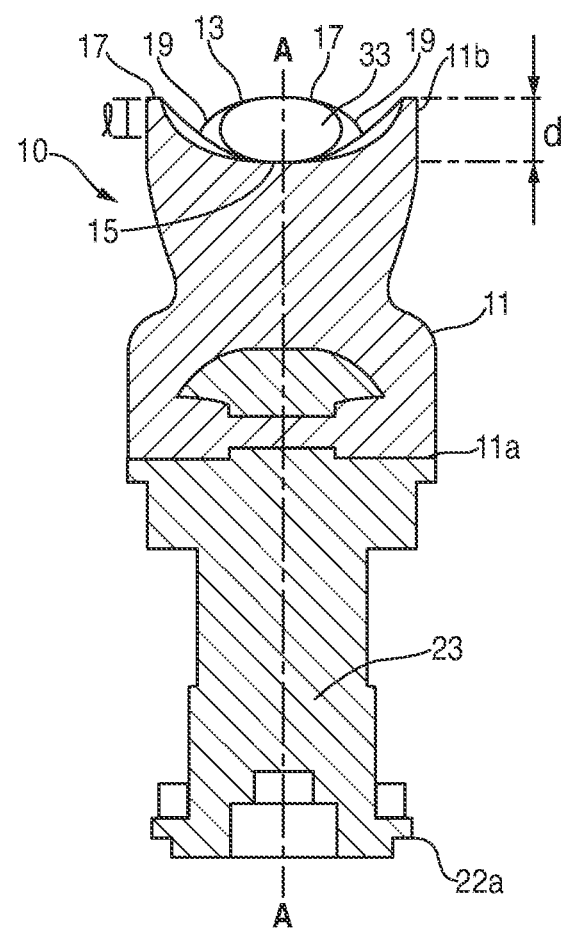

In the exemplary embodiment of FIGS. 8-10, the size, and therefore the shape, of the projections are different. In particular, the length l' of each recess 119 is approximately 1-2 mm while the depth d' of the cup to the center 115 of the cup 110 is approximately 3-4 mm. Therefore, the prophy cup 10 of FIGS. 3-5 is shallower than the prophy cup 110 and the prophy cup 110 of FIGS. 8-10 is flower-shaped as viewed from the top (FIG. 9) in contrast to the clover-shaped cup 10 of FIGS. 1-7.

Figure 11:
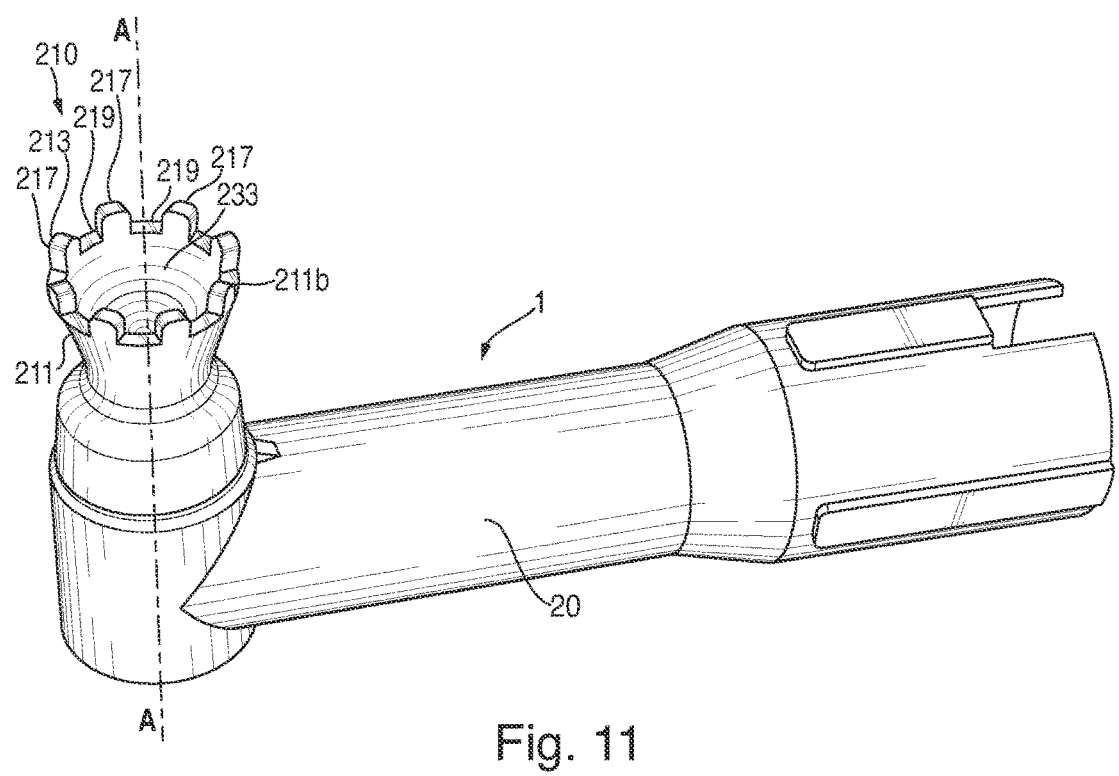
FIG. 11 is a perspective view of a prophy angle including a prophy cup according to a third embodiment of the invention.
Figure 12:
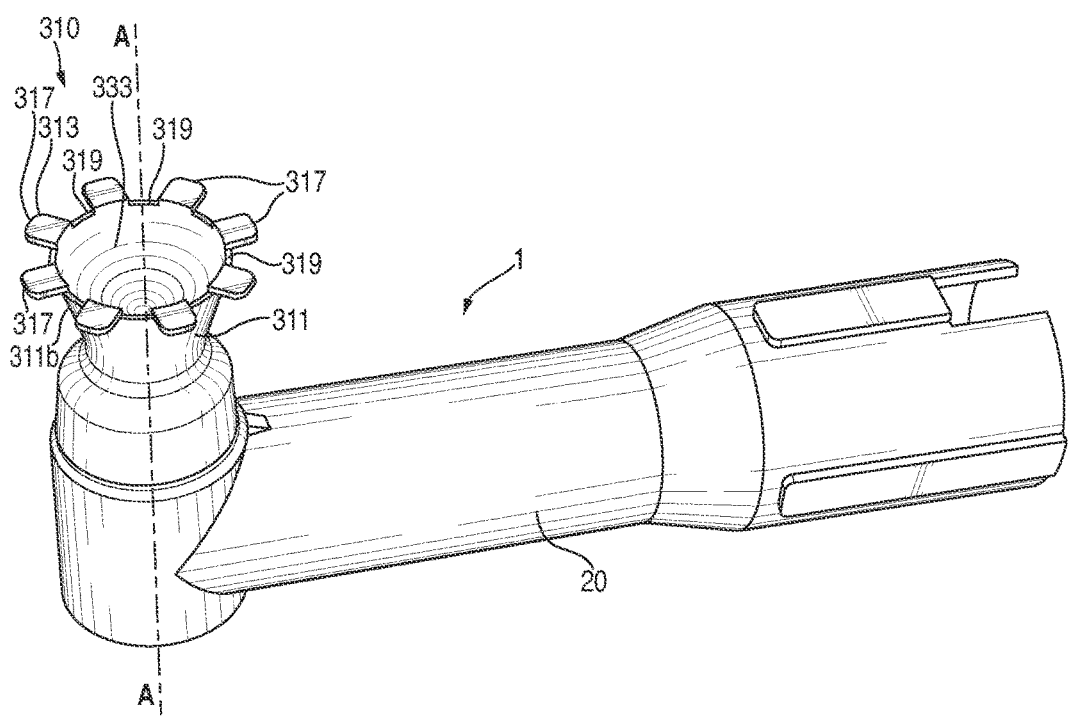
FIG. 12 is a perspective view of a prophy angle including a prophy cup according to a fourth embodiment of the invention.

In the exemplary embodiment of FIG. 11, the projections 217 of the prophy cup 210 have substantially rounded edges and are separated by recesses 219. The projections 217 are evenly disposed circumferentially at the second end 211b. In the embodiment of FIG. 11, the projections 217 are oriented substantially parallel to the axis A such that the projections 217 extend substantially axially relative to the longitudinal axis A. In additional or alternative embodiments, the projections 217 may also flare outwards and away from the axis as described above with respect to FIGS. 1-7. Additionally, it should be understood that the projections 217 may be oriented at angle between 0 degrees and 90 degrees relative to the longitudinal axis A. For example and as illustrated in the embodiment of FIG. 12, the projections 317 are oriented substantially perpendicular to the longitudinal axis A (i.e., 90 degrees relative to the axis A) such that the projections 317 extend substantially radially relative to the longitudinal axis A. Additionally, not all of the projections may be oriented the same, relative to the longitudinal axis A.

Regardless of the orientation, the projections 217, 317 are sufficiently flexible to expose the inner surface 233, 333 of the cup 210, 310 including projections 217, 317 against the surface of the tooth 30 when the cup 210, 310 is applied to the tooth 30 during cleaning. Advantageously, the projections 217, 317 are thin and flexible enough to fit comfortably between the tooth 30 and the surrounding gum 31 and under the gumline 32.

Figure 13:
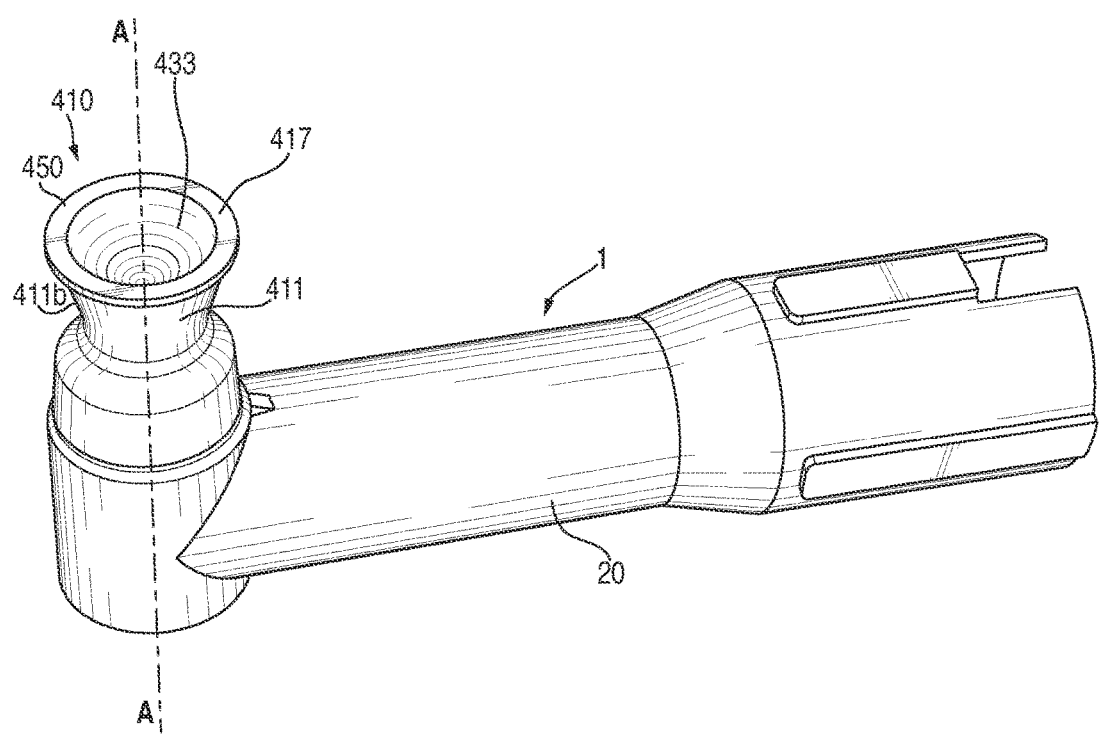
FIG. 13 is a perspective view of a prophy angle including a prophy cup according to a fifth embodiment of the invention.

FIG. 13 illustrates a prophy cup 410 in which the projection 417 at the second end of the wall 411 does not includes any recesses. As such, the projection 417 defines a continuous surface 450 that is configured to be pressed against the surface of the tooth 30 during cleaning. The surface 450 includes the abrasive material 34. Advantageously, the projection 417 is thin and flexible enough to fit comfortably between the tooth 30 and the surrounding gum 31 and under the gumline 32. In the illustrated embodiment, the projection 417 is substantially circular and centered around the longitudinal axis A. In additional or alternative embodiments, the projection 417 may define other shapes (i.e., a square or rectangle). The projection 417 is oriented substantially perpendicular to the axis A, although in additional or alternative embodiments the projection may be oriented at angle between 0 degrees and 90 degrees relative to the axis A.

While embodiments of the invention disclosed herein describe dental accessories or prophy angles, one skilled in art should recognize that alternative configurations may be employed without deviating from the scope of the invention.

The invention claimed is:

1. A prophylaxis angle configured to be attached to and operated by a powered dental handpiece, the prophylaxis angle comprising:
    a cup having a first end, a second end and a longitudinal axis, the first end couplable to the dental handpiece; and
    at least one projection at the second end of the cup;
    wherein the second end of the cup has a distal edge that does not lie in a single plane.

2. The prophylaxis angle according to claim 1, wherein the prophylaxis angle is disposable.

3. The prophylaxis angle according to claim 1, wherein the at least one projection is a plurality of projections.

4. The prophylaxis angle according to claim 3, wherein the cup has a longitudinal axis and each of the projections flare away from the longitudinal axis.

5. The prophylaxis angle according to claim 3, wherein the projections are sufficiently flexible and have a thickness sized to fit between a tooth and a gum and under a gumline.

6. The prophylaxis angle according to claim 3, wherein the projections have a substantially arcuately-shaped edge.

7. The prophylaxis angle according to claim 3, wherein the projections have substantially rounded edges.

8. The prophylaxis angle according to claim 3, wherein the cup has a longitudinal axis and the projections extend substantially axially from the second end.

9. The prophylaxis angle according to claim 3, wherein the cup has a longitudinal axis and the projections extend substantially radially from the second end.

10. The prophylaxis angle according to claim 1, further comprising an abrasive material on at least a portion of an inner surface of the cup.

11. The prophylaxis angle according to claim 1, wherein the abrasive material includes pumice.

12. A cup couplable to a prophylaxis angle, which in turn is couplable to a powered dental handpiece, the cup comprising:
    a first end engageable with the prophylaxis angle;
    a second end of the cup opposite the first end, the second end terminating in at least one projection;
    an inner surface, the inner surface being textured with an abrasive material suitable for polishing teeth.

13. The cup according to claim 12, wherein the at least one projection is a plurality of projections each separated by recesses.

14. The cup according to claim 13, wherein the cup has a longitudinal axis and each of the projections flare away from the longitudinal axis.

15. The cup according to claim 13, wherein the projections are sufficiently sized and flexible to fit between a tooth and a gum under a gumline.

16. The cup according to claim 13, wherein the projections are substantially scalloped-shaped.

17. The cup according to claim 13, wherein the projections are substantially rounded.

18. The cup according to claim 13, wherein the cup has a longitudinal axis and the projections extend substantially axially from the second end.

19. The cup according to claim 13, wherein the cup has a longitudinal axis and the projections extend substantially radially from the second end.

20. The cup according to claim 12, wherein the abrasive material is selected from the group consisting of pumice, perlite, aluminum oxide, aluminum-silicate, chalk, corundum, cuttle, diamond, emery, feldspar, garnet, Kieselguhr, quartz, silica, silicon carbide, sodium-potassium, tin oxide, Tripoli, and zirconium silicate.

21. The cup according to claim 12, wherein the prophylaxis angle is disposable.

22. The cup according to claim 12, wherein the prophylaxis angle is autoclavable.

23. The cup according to claim 12, wherein the cup is composed of a material selected from the group consisting of thermoplastic elastomer and silicone.

24. A method of manufacturing a prophylaxis cup, the method comprising:
    forming the prophylaxis cup;
    heating the prophylaxis cup to a predetermined temperature that softens the cup sufficiently to receive and retain an abrasive material; and
    pressing an inner surface of the prophylaxis cup into the abrasive material so that the abrasive material is retained on at least a portion of the inner surface of the cup.

25. The method of claim 24, wherein the abrasive material is selected from the group consisting of pumice, perlite, aluminum oxide, aluminum-silicate, chalk, corundum, cuttle, diamond, emery, feldspar, garnet, Kieselguhr, quartz, silica, silicon carbide, sodium-potassium, tin oxide, Tripoli, and zirconium silicate.

26. The method of claim 24, wherein forming the prophylaxis cup includes forming the prophylaxis cup of a material that softens when heated and creating projections at an end of the prophylaxis cup, the projections spaced apart by a plurality of recesses, wherein the projections have a thickness sized to fit between a tooth and a gum and under a gumline.

27. The method of claim 26, wherein only the projections have the abrasive material.

28. The method of claim 24 further comprising applying an adhesive to the inner surface of the cup prior to pressing an inner surface of the cup into the abrasive material.

29. The method of claim 28 wherein the adhesive is selected from the group consisting of heat curing adhesives, acrylic based ultraviolet cured adhesives, cyanoacrylate, urethanes, solvent based elastic polymer adhesives, and ethylene-vinyl acetate based hot melt adhesives.

* * * * *

UNITED STATES PATENT AND TRADEMARK OFFICE
CERTIFICATE OF CORRECTION

| | | |
|---|---|---|
| PATENT NO. | : 9,655,701 B2 | Page 1 of 1 |
| APPLICATION NO. | : 14/400621 | |
| DATED | : May 23, 2017 | |
| INVENTOR(S) | : Leoncio Angel Gonzalez et al. | |

It is certified that error appears in the above-identified patent and that said Letters Patent is hereby corrected as shown below:

On the Title Page

Under (73) Assignee, replace "Motorola Solutions, Inc., Schaumburg, IL (US)" with --Sunstar Americas, Inc., Schaumburg, IL (US)--

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*